(12) United States Patent
Voncken et al.

(10) Patent No.: US 10,575,715 B2
(45) Date of Patent: Mar. 3, 2020

(54) DEFLECTABLE MEDICAL DEVICE

(71) Applicant: KONINKLIJKE PHILIPS N.V., Eindhoven (NL)

(72) Inventors: Rudolf Maria Jozef Voncken, Eindhoven (NL); Jacob Roger Haartsen, Eindhoven (NL); Maurice Hubertus Elisabeth Van Der Beek, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 15/563,807

(22) PCT Filed: Mar. 31, 2016

(86) PCT No.: PCT/EP2016/057160
§ 371 (c)(1),
(2) Date: Oct. 2, 2017

(87) PCT Pub. No.: WO2016/156542
PCT Pub. Date: Oct. 6, 2016

(65) Prior Publication Data
US 2018/0078117 A1    Mar. 22, 2018

(30) Foreign Application Priority Data
Apr. 2, 2015  (EP) ..................................... 15162438

(51) Int. Cl.
*A61B 1/005*  (2006.01)
*A61M 25/01*  (2006.01)
(Continued)

(52) U.S. Cl.
CPC ......... *A61B 1/0058* (2013.01); *A61M 25/005* (2013.01); *A61M 25/0147* (2013.01);
(Continued)

(58) Field of Classification Search
CPC ....... A61B 1/0058; A61B 2017/00305; A61M 25/005
See application file for complete search history.

(56) References Cited

U.S. PATENT DOCUMENTS

| 5,090,956 A | * | 2/1992 | McCoy ................ A61B 1/0051 600/434 |
| 2006/0064055 A1 | * | 3/2006 | Pile-Spellman ........................... A61M 25/0105 604/95.05 |
| 2013/0204096 A1 | | 8/2013 | Ku |

FOREIGN PATENT DOCUMENTS

| EP | 2524645 A1 | 11/2012 |
| JP | H0349767 A | 3/1991 |

(Continued)

*Primary Examiner* — Rebecca E Eisenberg
*Assistant Examiner* — Melissa A Snyder

(57) ABSTRACT

A deflectable medical device (1) includes a shape memory alloy wire (15) integrated into a flexible elongated body (11). The shape memory alloy wire (15) is arranged to shorten upon receiving energy from an energy supply (2,4), thereby deflecting the medical device (1). A rod (18) positioned in a lumen (14) of the flexible elongated body (11) and compressed between a fixture (16) in the proximal end (12) of the elongated body (11) and the distal end (13) of the elongated body (11) is responsible for the shape memory alloy wire (15) recovering its initial length upon discontinuation of energy supply.

12 Claims, 10 Drawing Sheets

(51) Int. Cl.
*A61M 25/00* (2006.01)
*A61B 17/00* (2006.01)
*A61B 18/14* (2006.01)

(52) U.S. Cl.
CPC ..... *A61M 25/0158* (2013.01); *A61B 18/1492* (2013.01); *A61B 2017/00305* (2013.01); *A61B 2017/00318* (2013.01)

(56) References Cited

FOREIGN PATENT DOCUMENTS

| | | |
|---|---|---|
| JP | H05163 A | 1/1993 |
| JP | 2001258827 A | 9/2001 |
| WO | 9214506 A1 | 9/1992 |
| WO | 2007013545 A1 | 2/2007 |

* cited by examiner

DEFLECTABLE MEDICAL DEVICE

CROSS-REFERENCE TO PRIOR APPLICATIONS

This application is the U.S. National Phase application under 35 U.S.C. § 371 of International Application No. PCT/EP2016/057160, filed on Mar. 31, 2016, which claims the benefit of European Patent Application No. 15162438.4, filed on Apr. 2, 2015. These applications are hereby incorporated by reference herein.

FIELD OF THE INVENTION

The present invention relates to a medical device with controllable deflection of a portion of the medical device, a system comprising the medical device and a method for deflecting a medical device.

BACKGROUND OF THE INVENTION

Minimally invasive procedures involve accessing specific sites through anatomical structures. Examples of such procedures are angioplasty, stenting, thrombolysis, where an interventional device is navigated through the vasculature to access a designated site. Navigating through branching pathways is challenging without appropriately designed steerable medical devices.

A medical device with a steerable distal portion is disclosed in U.S. Pat. No. 5,090,956, wherein the maneuverability of the distal portion is achieved by a combination of a temperature activated memory element moving in a first direction to assume a predetermined shape when heated to a predetermined temperature and a spring for yieldable urging the shape memory element in a second direction away from the first direction upon cooling of the memory element to a temperature less than the predetermined temperature, so that the memory element is moved to assume a shape other than the predetermined shape.

Multidirectional steering of such medical device can be achieved by integrating multiple temperature activated memory elements, each of them being able to assume a predetermined shape when heated to a predetermined temperature. Deflection of a device with such configuration occurs due to the mechanical equilibrium of the force generated by the first temperature activated memory element moving in a first direction to assume a predetermined shape, the restoring force of the spring and the restoring forces of the non-active memory elements. Such construction becomes complex with increasing maneuverability requirements due to the fact that the force necessary to be created by a first temperature activated memory element in order to overcome the restoring forces of the spring and the remaining non-activated memory elements is significantly large, resulting in a considerably large cross sectional area of the temperature activated memory element. This however works against miniaturization of the device, hence when a second temperature activated memory element is required to deflect the device in a second direction to assume a predetermined shape of the second temperature activated memory element, the large cross section area of the first element creates a large restoring force at its turn, which limits the bending radius of the device.

SUMMARY OF THE INVENTION

It is an object of the invention to provide a medical device with improved potential for miniaturization.

According to the invention, this object is realized by a medical device comprising:
a flexible elongated body having proximal and distal ends and a first lumen,
a shape memory alloy wire eccentric to the longitudinal axis and extending at least partially along the elongated body, the shape memory alloy wire fixed at least at two distinctive points with respect to the elongated body and arranged to receive energy from an energy supply so as to heat the shape memory alloy wire,
a fixture in the proximal end of the elongated body,
a rod located in the first lumen and extending at least from the fixture to the distal end of the elongated body, the rod fixed with respect to the elongated body between the fixture and the distal end;
wherein the rod is compressed between the fixture and the distal end of the elongated body,
wherein the shape memory alloy wire is arranged to shorten upon receiving energy from the energy supply.

The benefit of using wires of shape memory alloys is the miniaturization potential of the medical device, since the operation of the medical device relies on the lever that is created by the shape memory alloy wire positioned eccentric to the longitudinal axis of the medical device, and arranged to shorten upon receiving energy from the energy supply. There is no need of a restoring force of a spring or that of supplementary structures urging the shape memory element in a second direction away from the first direction upon cooling of the memory element to a temperature less than the predetermined temperature, since the deflection is not created by the bending force of a shape memory element.

The shape memory alloy wire requires axial tension to regain its initial length after discontinuing supply of energy to the shape memory alloy wire, a process called detwinning, attributed to the unique deformation mechanism partially responsible for the shape memory effect in addition to phase transformation. A rod located in a first lumen and extending from a fixture in the proximal end of the elongated body to the distal end of the elongated body, and arranged such that the rod is compressed between the fixture and the distal end of the elongated body, is responsible for detwinning the shape memory alloy wire. The rod arranged in a compressed status creates tensile stress in the elongated body, which brings the shape memory alloy wire back to its initial length upon discontinuation of energy supply to the shape memory alloy wire. A significant advantage of the invention is that there are less stringent spatial requirements for creating axial detwinning forces than for creating lateral restoring bending forces. Improvement in deflection performance of the medical device according to the invention are the smaller radius of bending with respect to a medical device with shape memory alloy elements bending laterally and better reproducibility of the steering performance.

In an embodiment, the medical device is further adapted such that the compression of the rod is adjustable through the fixture in the proximal end of the elongated body.

In another embodiment of the medical device, the elongated body of the medical device may comprise a second lumen, wherein the shape memory alloy wire can be arranged. The shape memory alloy wire may be fixed only at its both ends with respect to the elongated body, allowing free movement of the shape memory alloy wire along the rest of its length with respect to the elongated body. The friction between the elongated body and the shape memory alloy wire can significantly be reduced during operation of the medical device, creating an even larger range of bending radii addressable by the medical device.

Numerous principles may be used for heating the shape memory alloy wire. In an embodiment according to the invention, the medical device comprises a resistor connectable to an energy supply and arranged to convert the electrical energy provided by the energy supply in heat for heating the shape memory alloy wire. The resistor may be a metallic wire placed in the surrounding of the shape memory wire, or it may be a metallic structure coaxial with the shape memory alloy wire. Alternatively, the shape memory alloy wire may be provided with a conformal metallic coating as resistor. The latter has that advantage that the lateral dimension necessary for the energy source can be minimized, since the thickness of such coating is sufficient in the micrometer range.

In another embodiment according to the invention the shape memory alloy wire can be adapted to be connectable to the energy supply and arranged to convert electrical energy provided by the energy supply in heat. The benefit of directly connecting the shape memory alloy wire to the energy supply is that no additional internal energy source is necessary to be positioned in the surrounding of the shape memory alloy wire, since the heating of the shape memory alloy wire can be obtained by its own resistive heating.

In yet another embodiment according to the invention the medical device comprises additional lumens in the elongated body, extending at least partially along the shape memory alloy wire. The lumens, adapted to be connectable to a pump for providing fluid flow, may be connected with each other at their distal ends. The fluid flow can significantly improve the response of the medical device by accelerating the recovery of the medical device to its neutral position when providing energy to the shape memory alloy wire discontinues. Alternatively, the pump can be used as energy supply, providing fluid flow in the lumens at higher temperature than that of the shape memory alloy wire, thereby facilitating heat transfer from the fluid to the shape memory alloy wires so as to heat the shape memory alloy wire.

A medical device may comprise multiple shape memory alloy wires extending at least partially along the elongated body, having initial lengths and being fixed at both ends with respect to the elongated body. Deflection of the medical device in multiple directions can be achieved when the shape memory alloy wires are arranged to receive dissimilar quantities of energy from the energy supply. Depending on the combination of the quantities of energies received by the shape memory alloy wires, the radii of bending of the medical device can practically be achieved in any direction with respect to the longitudinal axis of the medical device.

In yet a further embodiment, the elongated body of the medical device comprises segments with various stiffness, and the shape memory alloy wires extend at least partially along two adjacent segments with different stiffness. The benefit of such configuration is the potential for deflecting a medical device in a complex three-dimensional shape.

In a further aspect of the invention a system is presented comprising the deflectable medical device, an energy supply and a control unit. The control unit is arranged to control the quantity of energy provided by the energy supply to the shape memory alloy wire in the medical device. The control unit and the energy supply may be integrated in one unit. The system may further comprise a pump for circulating fluid through the lumens specifically designated therefore in the medical device. The pump may also be controlled by the control unit with respect to supplying fluid flow for the medical device at required temperature and volumetric flow rate.

In another aspect of the invention a method for deflecting a medical device is presented, the method comprising:

providing a compression to a rod fixed between a distal end and a fixture in a proximal end of an elongated body of a deflectable medical device, the medical device further comprising one or multiple shape memory alloy wires arranged eccentric to the longitudinal axis of the elongated body, extending at least partially along the elongated body and fixed at both ends with respect to the elongated body, providing energy to the one or multiple shape memory alloy wires by an energy supply. The method according to the invention allows lateral bending of the medical device due to the axial stroke of the shape memory alloy wires positioned eccentric with respect to the longitudinal axis of the medical device. The method may further comprise a step for providing fluid flow in a third lumen in the elongated body of the medical device, thereby improving the response time of the medical device to discontinuation of energy supplied to the shape memory alloy wires and accelerate the recovery of the medical device to its neutral position.

Additional aspects and advantages of the invention will become more apparent from the following detailed description, which may be best understood with reference to and in conjunction with the accompanying drawings.

DETAILED DESCRIPTION OF EMBODIMENTS

Figure 1:
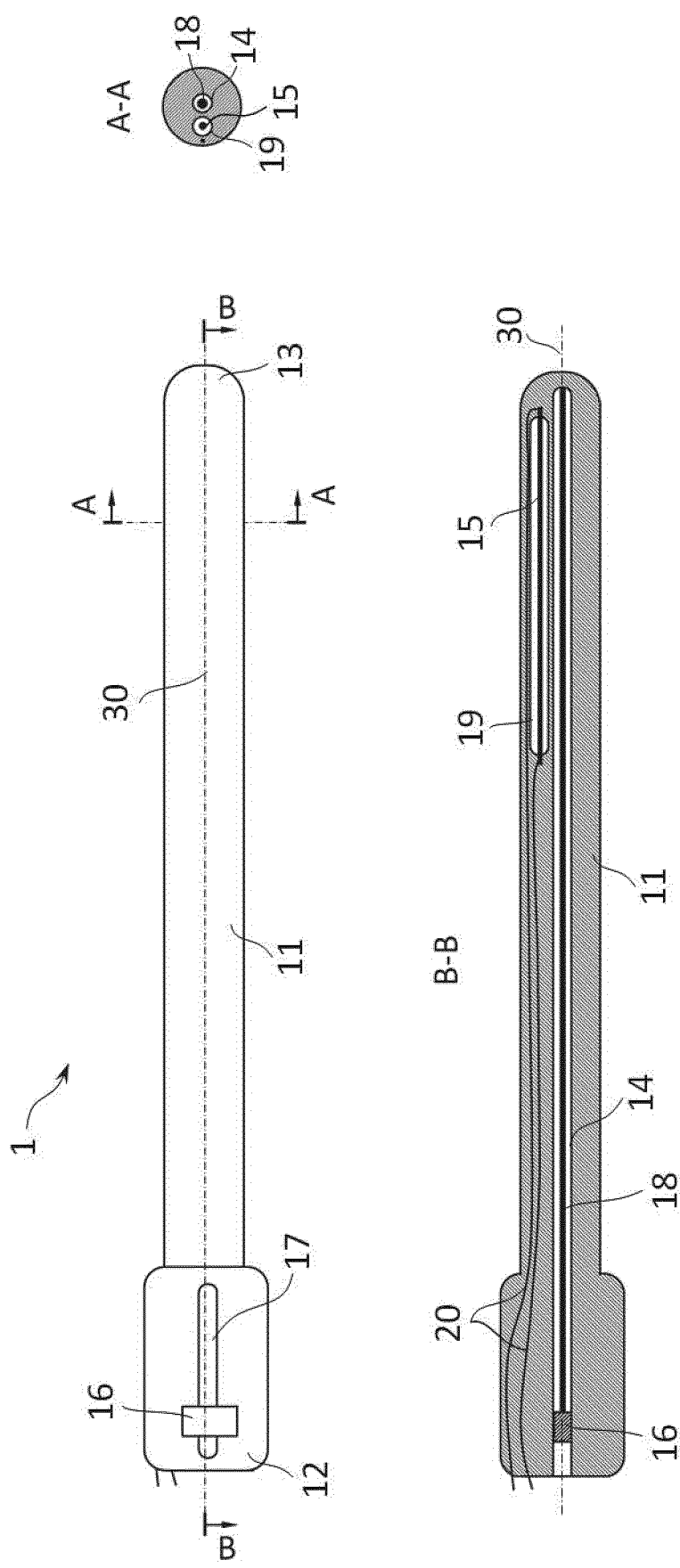
FIG. 1 shows schematically and exemplarily an embodiment of a medical device according to the invention.
Figure 2:
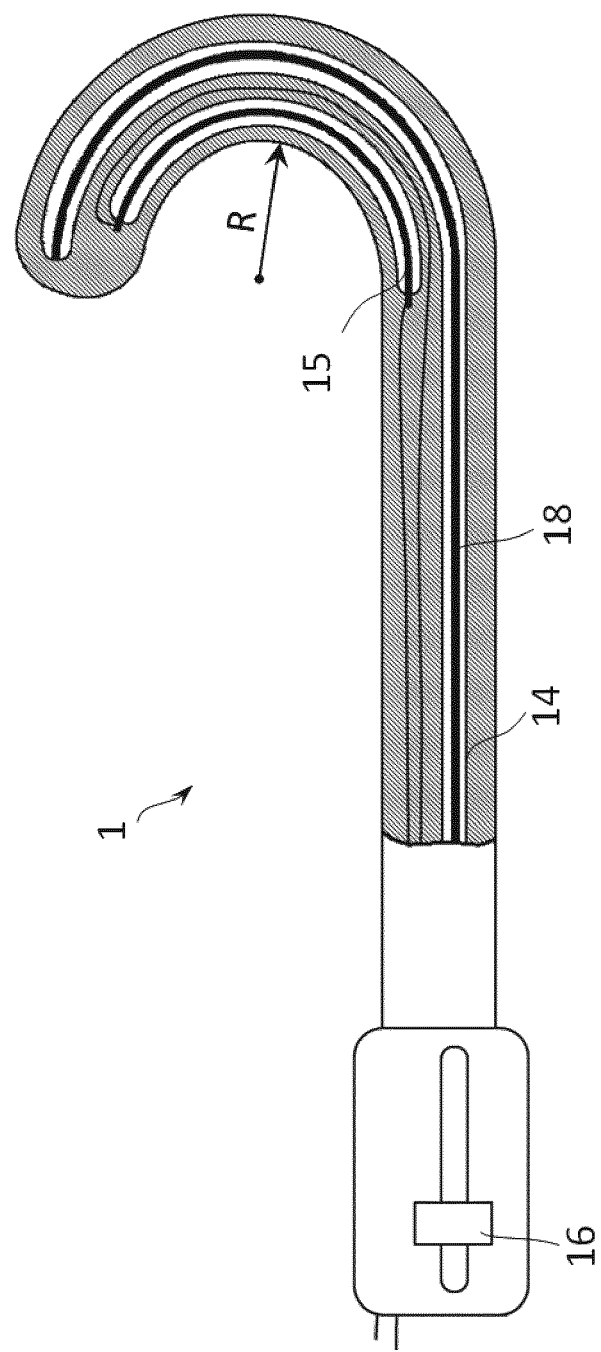
FIG. 2 shows schematically and exemplarily the medical device with deflected distal portion.

Navigation of medical devices through branching pathways sets stringent requirement with respect to device configuration. Besides reduced diameter and flexibility of the medical devices, steering of the distal portion is utmost important for the ability of reaching designated locations within anatomical structures. FIG. 1 shows an embodiment of a medical device 1 according to the invention. The medical device 1 is constructed from a flexible elongated body 11 having a proximal end 12 and a distal end 13, comprising a first lumen 14 visible in the longitudinal cross section B-B of the medical device, wherein a rod 18 is positioned. The rod may consist of compressible or incompressible materials. The proximal end 12 of the elongated body 11 comprises a fixture 16, the rod 18 extending from the fixture 16 to the distal end 13 of the elongated body 11. The proximal end 12 of the elongated body may be a handgrip. The functional designation of the fixture 16 is fixing and/or supporting the rod directly or indirectly, such that the rod 18 can be brought in a compression state between the fixture 16 and the distal end 13 with respect to the elongated body 11. The position of the fixture 16 may be variable with respect to the handgrip by sliding the fixture 16 through a slot 17. The fixture 16 may alternatively be a spindle mechanism. Depending on the mechanism used for the fixture, the rod 18 may extend proximally beyond the fixture 16 or even beyond the medical device 1. The rod 18 is arranged such that it is compressed between the fixture 16 and the distal end 13 of the elongated body 11, thereby generating a tensile stress in the elongated body 11. The fixture 16 may further comprise a loaded spring supporting the rod 18. The first lumen 14 may be positioned coaxially in the medical device as shown in FIG. 1, or it may be eccentric to the longitudinal axis, like in the FIG. 2.

A shape memory alloy wire 15, visible in the transversal cross section A-A and in the longitudinal cross section B-B, is arranged in a second lumen 19, extending at least partially along the elongated body 11 and positioned eccentric to the longitudinal axis 30 of the elongated body 11. Both ends of the shape memory alloy wire are fixed with respect to the elongated body 11. The shape memory alloy wire 15 is arranged to receive energy from an energy supply through wiring 20 connected to the proximal and distal ends of the shape memory alloy wire 15. By supplying electrical energy to the shape memory alloy wire, its temperature rises due to resistive heating.

The shape memory alloy wire 15, having an initial length, is arranged to shorten upon its resistive heating, which creates a pulling force on the elongated body 11 at the locations where both ends of the shape memory alloy wire 15 are fixed with respect to the elongated body 11. This creates a deflection of the portion of the elongated body 11 associated to the position of the shape memory alloy wire 15, due to the eccentric position of the second lumen 19 to the longitudinal axis 30 of the medical device 1. The longitudinal axis 30 is defined as the line connecting the centers of the transversal cross sections along the length of the medical device 1 in the neutral position, thus when there is no energy provided to the shape memory alloy wire. The radius of deflection R depends on the materials used for the manufacturing of the medical device 1, as well as on the design configuration. Usual candidates for the shape memory alloy wires are alloys of Ni—Ti, Cu—Al—Ni, Cu—Zn, Ni—Ti—Pd with typical diameters of 50-200 micrometers. A broad range of polymers can be used for fabrication of the elongated body, from which the most known group is that of thermoplastic elastomers (e.g. PEBAX).

The benefit of using wires of shape memory alloys is the miniaturization potential of the medical device, since relatively thin shape memory alloy wires create sufficiently high force in axial stroke upon heating. The operation of the medical device relies on the lever that is created by the shape memory alloy wire positioned eccentric to the longitudinal axis 30 of the medical device, therefore a restoring bending force of a spring or that of supplementary structures, urging the shape memory element in a second direction away from the first direction upon cooling of the shape memory alloy wire, is not necessary. However, the shape memory alloy wire 15 requires axial tension to regain its initial length after discontinuing supply of energy to the shape memory alloy wire 15. Detwinning, the particular deformation mechanism partially responsible for the shape memory effect in addition to phase transformation, is promoted by the axial tension generated in the elongated body 11 due to the compression of the rod 18 between the fixture 16 and the distal end 13. Detwinning shape memory alloy wires in axial direction is less stringent and requires only sufficient axial tension in the elongated body, which allows manufacturing of medical devices with smaller diameter than those needing detwinning of laterally bending shape memory elements.

Figure 3:
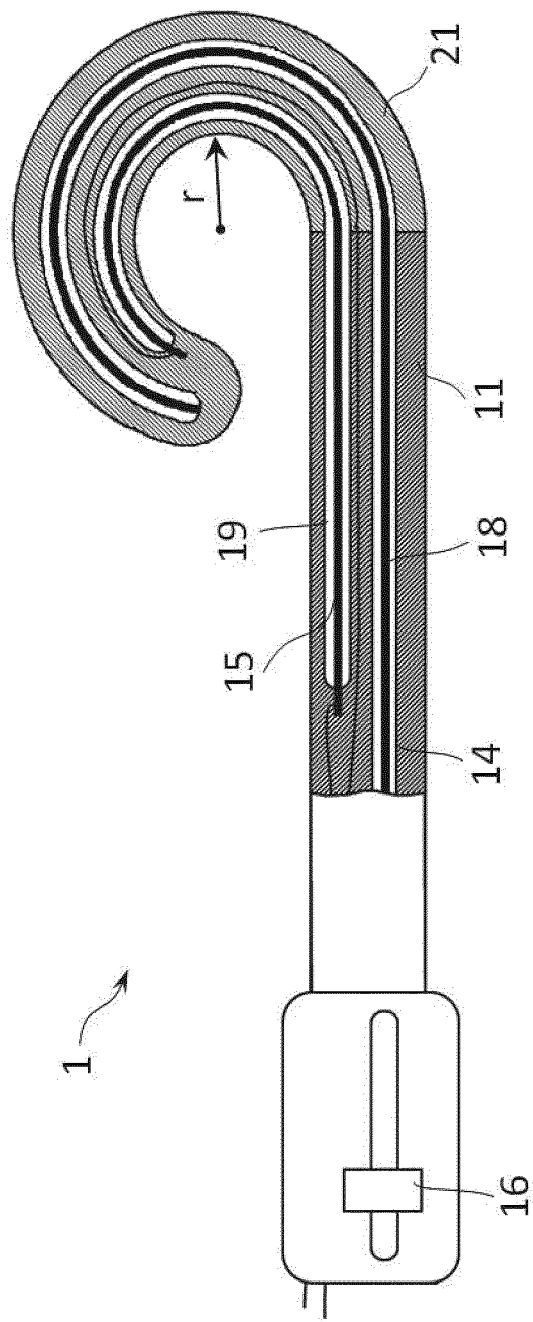
FIG. 3 shows schematically and exemplarily an embodiment of the medical device with deflected distal portion, the medical device comprising heterogeneous elongated body.

In the embodiment of the medical device shown in FIG. 3, the elongated body of the medical device is heterogeneous, specifically it is constructed from two materials with different properties. The proximal part of the elongated body 11 is made of a stiffer polymer which can additionally be reinforced with braiding to confer higher rigidity of the proximal portion of the medical device. The distal part 21 of the elongated body can be made of a more flexible polymer, as mostly the distal part of the medical device has different requirements in order to easily be deflectable when navigating in branching anatomical structures. The second lumen 19 extends at least partially in both segments of the elongated body, in the stiffer proximal part 11 and in the flexible distal part 21. The shape memory alloy wire 15, located in the second lumen 19 and fixed at both ends with respect to the heterogeneous elongated body, can be considerably long. A shape memory alloy wire of a certain material, hence with a defined maximum allowable strain, can produce a larger axial stroke for a longer segment when it is exposed to a difference of temperature. The deflection of the medical device due to the axial stroke created by the shortening of the shape memory alloy wire will not have its effect in the stiffer part, but the effect will be transferred almost entirely to the flexible distal part, resulting in a smaller radius of deflection r of the distal part of the medical device 1. In another embodiment of the medical device the stiffer and flexible regions of the elongated body may alternate repeatedly along the length of the medical device, resulting in complex three dimensional deflection of the medical device in operation.

Figure 4:
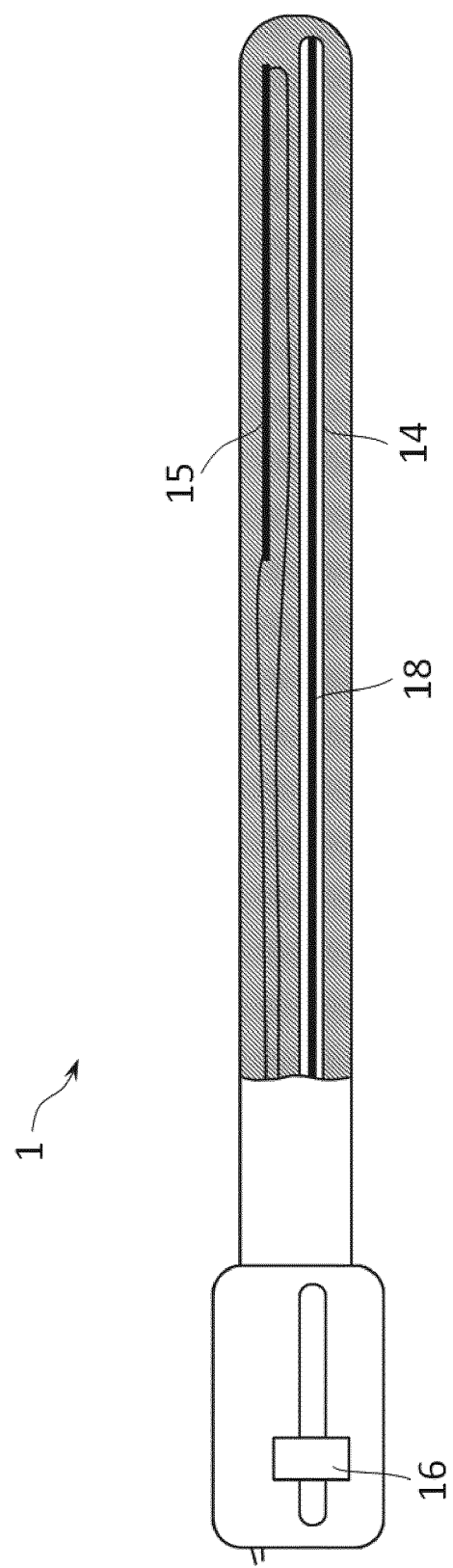
FIG. 4 shows schematically and exemplarily an embodiment of the medical device with shape memory alloy wire embedded into the elongated body.

The second lumen 19 in the elongated body is not directly necessary for deflecting a medical device, therefore the shape memory alloy wire 15 may directly be integrated in the elongated body, as shown in FIG. 4. The requirement for deflecting the medical device is that an axial stroke of the shape memory alloy wire 15 is created with respect to the longitudinal axis of the elongated body 11. Therefore, the shape memory alloy wire has to be fixed at least in two distinctive points with respect to the elongated body 11. Technology like overmolding allows incorporation of the shape memory alloy wire in the elongated body. When multiple contact points or regions exist between the elongated body 11 and the shape memory alloy wire 15 along their overlapping length, the friction between the two can be significant during relative motion occurring by deflection of the medical device. This can potentially limit the range of bending radii addressable by the medical device. Processing steps such as covering portion of the shape memory alloy wire with materials promoting low friction is a practical solution.

The shape memory alloy wire may be arranged to receive energy from an energy supply in numerous alternative ways.

Figure 5:
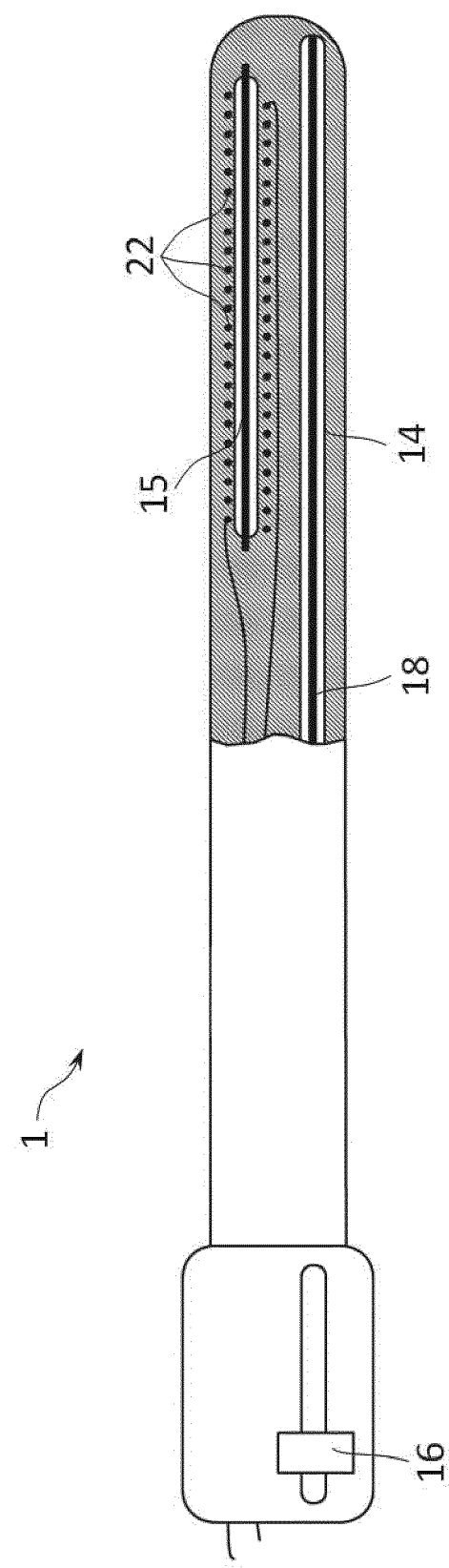
FIG. 5 shows schematically and exemplarily an embodiment of the medical device with resistor positioned in the surrounding of the shape memory alloy wire.

In an embodiment of the medical device 1 shown in FIG. 5, the elongated body 11 comprises a resistor connectable to an energy supply and arranged to convert the electrical energy received from the energy supply in heat for heating the shape memory alloy wire. The resistor may comprise windings 22 of metallic wire around the shape memory alloy wire 15, or it may be a metallic wire placed in the surrounding of the shape memory alloy wire. Alternatively, the resistor may be metallic structure coaxial with the shape memory alloy wire. This can be realized by conformal metallic coating of the shape memory alloy wire through various technological procedures (e.g. evaporation, electroplating, etc.).

A coil surrounding the shape memory alloy wire may also be used for induction heating of the shape memory alloy wire 15. Such embodiment may be similar to that presented in FIG. 5, wherein the induction coil 22 can be operated with a high-frequency alternative current.

The energy supply might be a pump circulating fluid in the surrounding of the shape memory alloy wire 15, the fluid having a higher temperature than the shape memory alloy wire. In a medical device with such a configuration, shown in FIG. 6, the shape memory alloy wire 15 receives energy from the fluid through heat transfer. A third lumen 23 and a fourth lumen 24 in the elongated body 11 are connected with each other in the distal portion of the elongated body, and they extend such that at least partially overlap in the axial direction with the shape memory alloy wire 15. The third lumen 23 is adapted to allow fluid inflow and the fourth lumen 24 to allow fluid outflow. The wiring 20 of the shape memory alloy wire 15 is superfluous and might be absent when fluid at higher temperature than that of the shape memory alloy is circulated for heating the shape memory alloy wire 15.

Figure 6:
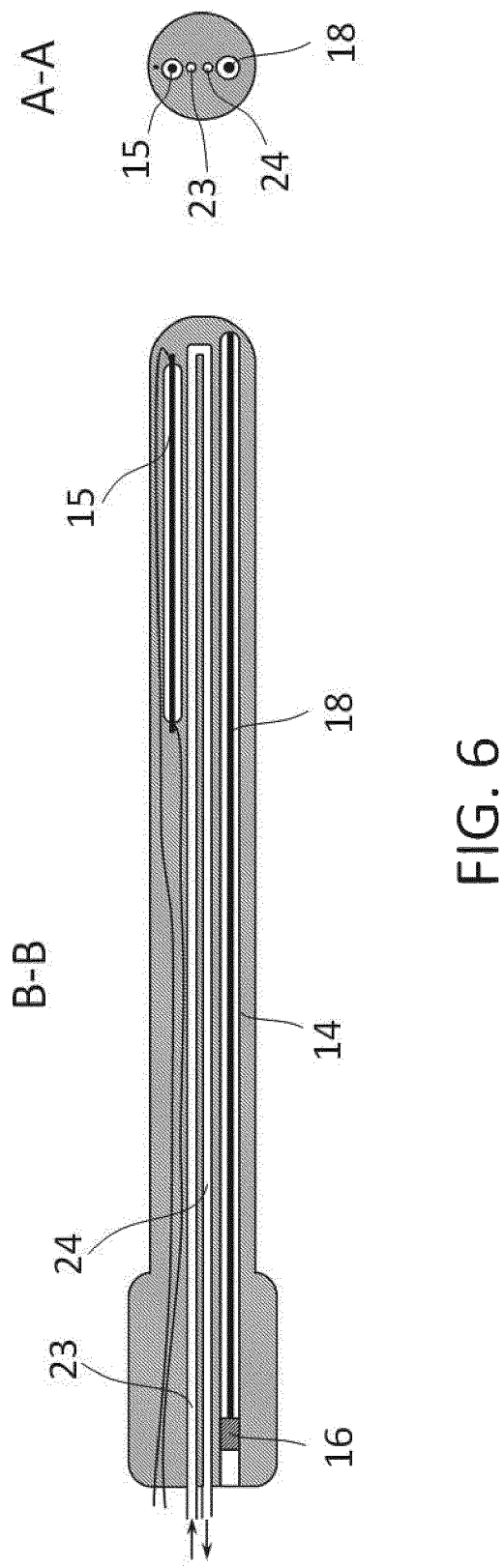
FIG. 6 shows schematically and exemplarily an embodiment of the medical device with lumens in the elongated body adapted for fluid flow.

The medical device shown in FIG. 6 can alternatively be configured such that the shape memory alloy wire 15 receives electrical energy through the wiring 20 from the energy supply, and fluid at a lower temperature than that of the shape memory alloy wire 15, flowing through the third and fourth lumens 23,24, cools the shape memory alloy wire. The cooling fluid flow can significantly shorten the response time of the medical device to discontinuation of supplying energy to the shape memory alloy wire, thereby accelerating the recovery of the medical device to its neutral position.

Figure 7:
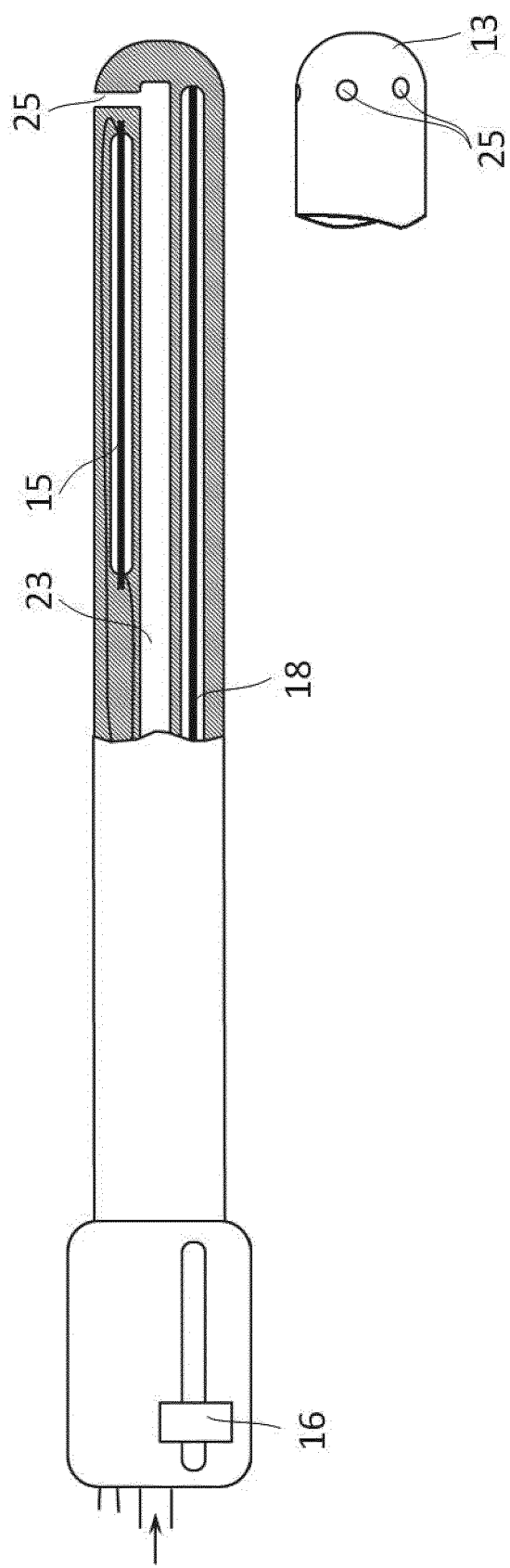
FIG. 7 shows schematically and exemplarily an embodiment of the medical device comprising a lumen for fluid flow and fluid dispensing holes in the distal portion.

In an alternative embodiment of the medical device shown in FIG. 7, the elongated body comprises just the third lumen 23, adapted only for fluid inflow. The third lumen 23 communicates with through-holes 25 in the distal portion 13 of the elongated body. The fluid flowing through the third lumen 23 is dispensed into the surrounding of the distal end 13 via the through-holes 25. Cooling of the shape memory alloy wire 15 with this configuration is advantageous for medical devices where irrigation with fluid is required (e.g. cardiac ablation).

Figure 8:
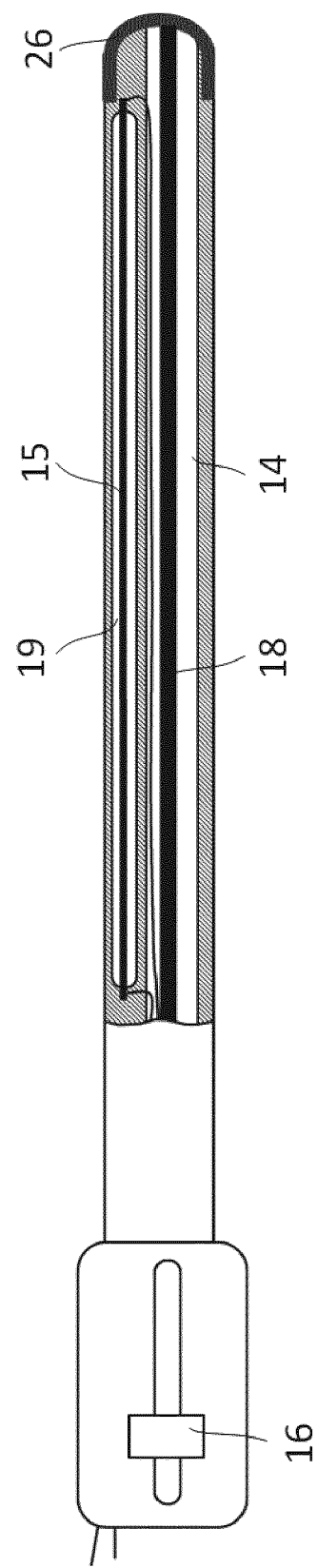
FIG. 8 shows schematically and exemplarily an embodiment of the medical device with a metallic distal end.

FIG. 8 shows a medical device with distal portion ending with a metallic tip 26 for providing energy to the surrounding. In cardiac ablation the surrounding is heart tissue and the energy may be radiofrequency current delivered by a platinum-iridium alloy tip. The rod 18 can be supported by the metallic tip 26 at the distal end 13, or it can be fixed to it. In yet a further alternative, the rod 18 may be used as electrical connection of the metallic tip to the external radiofrequency current source.

Figure 9A:
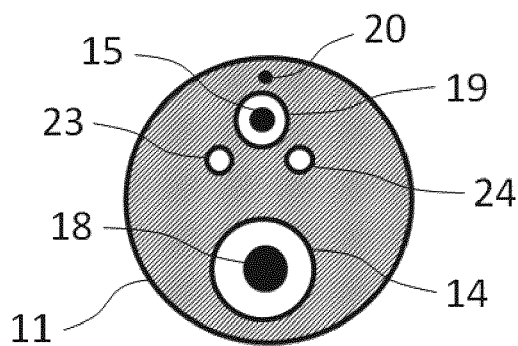
FIGS. 9a, 9b show transversal cross sections of alternative embodiments of the medical device.
Figure 9B:
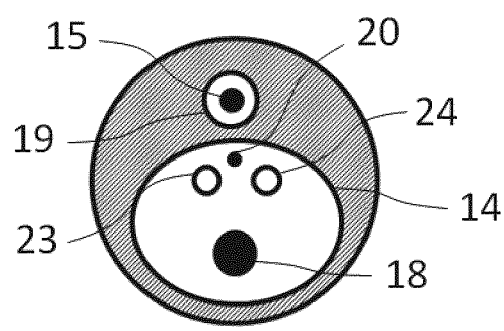

Combination of the aforementioned embodiments may provide optimal solution for specific applications. The position of various components of the medical device may also vary. In the transversal cross section of a medical device, shown in FIG. 9a, the third and fourth lumens 23,24 adapted for fluid flow are at equal distance to the shape memory alloy wire 15, thereby further accelerating the recovery of the medical device to its neutral position upon discontinuation of supplying energy to the shape memory alloy wire. FIG. 9b shows an embodiment with a first lumen 14 having a larger cross section, wherein besides the rod 18 also the wiring 20 of the shape memory alloy wire as well as the third 23 and fourth 24 lumens are placed. The main advantage is an easier manufacturing of such a medical device.

Figure 9C:
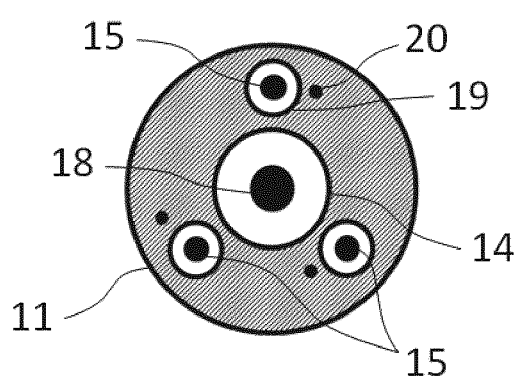
FIGS. 9c, 9d show transversal cross sections of alternative embodiments of the medical device comprising multiple shape memory alloy wires.
Figure 9D:
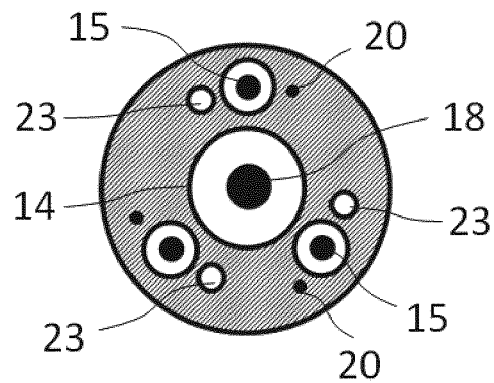

Multiple shape memory alloy wires extending at least partially along the elongated body may be used in a medical device in order to increase the maneuverability of the medical device in multiple directions and/or to deflect differentially various segments of the medical device. In FIG. 9c a transversal cross section of an embodiment of the medical device is shown, comprising three shape memory alloy wires 15, allowing deflection of the distal portion of the medical device in any direction with respect to its longitudinal axis 30 by an appropriately harmonized operation of the individual shape memory alloy wires with dissimilar quantities of energy from the energy supply. In an alternative embodiment the medical device with multiple shape memory alloy wires 15 may have individual cooling lumens 23 for each shape memory alloy wire 15, as shown in FIG. 9d.

Figure 10:
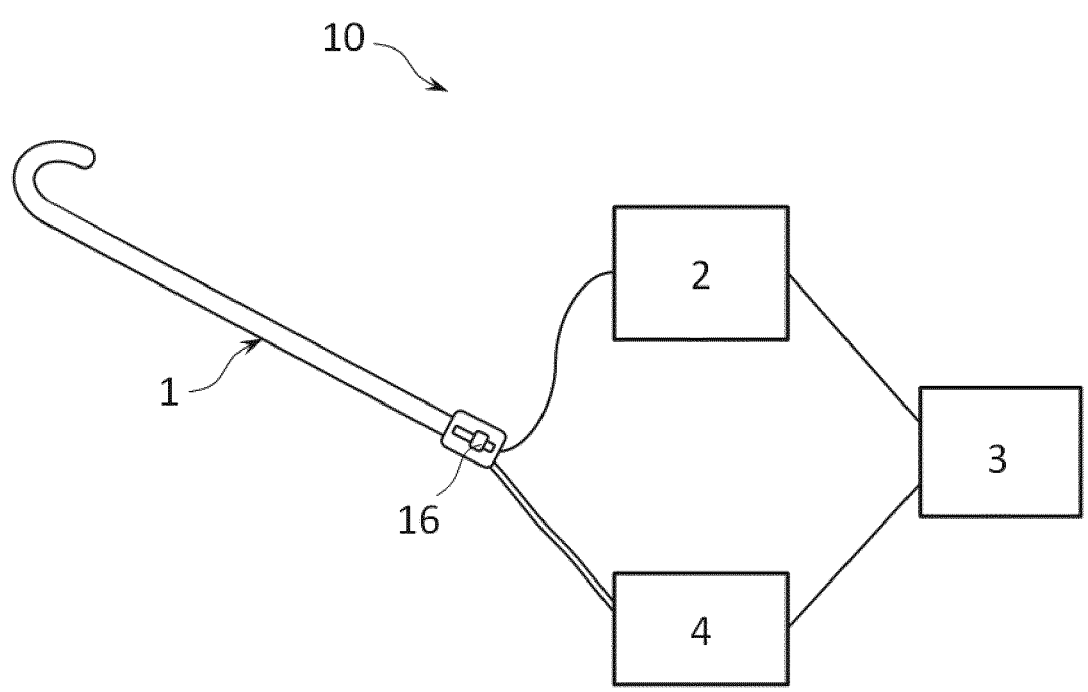
FIG. 10 shows schematically and exemplarily a system for deflection of a medical device according to the invention.

The deflection of the medical device needs to be controlled and reproducible for navigation within complex anatomical structures. A system 10 assuring reproducible deflection performance of the medical device is shown in FIG. 10. A control unit 3 is regulating the quantity of energy provided by the energy supply 2 to the shape memory alloy wire in the medical device 1. The control unit 3 and the energy supply 2 may be integrated in one unit. The system 10 may further comprise a pump 4 for circulating fluid through the lumens specifically designated therefore within the medical device 1. The pump 4 may also be controlled by the control unit 3 with respect to supplying fluid flow for the medical device at required temperature and volumetric flow rate. The pump may function in two regimes. The first regime is for cooling the shape memory alloy wires, therewith shortening the reaction time of the shape memory alloy wires to an alteration of the quantity of energy received from the electrical energy source 2. Alternatively, the pump 4 may also function as energy supply by providing fluid flow in the lumens at a higher temperature than that of the shape memory alloy wire, thereby transferring heat from the fluid in the lumens to the shape memory alloy wire positioned adjacent to the lumens in the medical device. The control unit 3 may further control the compression of the rod 18 between the fixture 16 and the distal end 13 of the medical device 1. The fixture 16 may be an electrically controllable spindle mechanism.

Controlling the deflection of the medical device comprising one or multiple shape memory alloy wires extending at least partially along the elongated body can be realized in steps. In a first step the control unit 3 provides a finite compression to the rod 18 fixed between the distal end 13 and the fixture 16 of the deflectable medical device 1. In the second step the control unit 3 regulates the quantity of energy necessary for the one or multiple shape memory alloy wires 15 to deflect the medical device 1 according to the required performance, and the energy supply 2 provides the respective quantity of energy to the one or multiple shape memory alloy wires 15. In step three the control unit 3 regulates the parameters of the pump 4 with respect to temperature of the fluid and volumetric fluid flow rate, according to the required deflection performance of the medical device 1. The steps may be carried out consecutively or simultaneously.

The control unit comprises a computer, a computer-readable medium having stored a computer-executable program and a user interface. The computer program comprises program code means for causing a deflectable medical device to carry out the steps for deflection of the medical device when the computer program is run on the computer of the control unit controlling the deflectable medical device.

Although medical device was used in the exemplary description of the invention, that should not be construed as limiting the scope.

Other variations to the disclosed embodiments can be understood and effected by those skilled in the art in practicing the claimed invention, from a study of the drawings, the disclosure, and the appended claims.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. A deflectable medical device comprising:
   a flexible elongated body having proximal and distal ends and a first lumen;
   a shape memory alloy wire eccentric to the longitudinal axis and extending at least partially along the elongated body, the shape memory alloy wire fixed at least at two distinctive points with respect to the elongated body and arranged to receive energy from an energy supply so as to heat the shape memory alloy wire;
   a fixture in the proximal end of the elongated body; and
   a rod located in the first lumen and extending at least from the fixture to the distal end of the elongated body, the rod fixed with respect to the elongated body between the fixture and the distal end,
   wherein the rod is compressed between the fixture and the distal end of the elongated body,
   wherein the shape memory alloy wire is arranged to shorten upon receiving energy from the energy supply,
   wherein the elongated body comprises a second lumen, and
   wherein the shape memory alloy wire is located in the second lumen and fixed at both ends with respect to the elongated body.

2. The medical device according to claim 1, wherein the shape memory alloy wire is connectable to an energy supply and arranged to convert electrical energy provided by the energy supply into heat.

3. The medical device according to claim 1, the medical device comprising a third lumen in the elongated body extending at least partially along the shape memory alloy wire, the third lumen connectable to a pump for providing fluid flow in the third lumen.

4. The medical device according to claim 3, the medical device comprising a fourth lumen in the elongated body extending at least partially along the shape memory alloy wire, the third and the fourth lumens connected with each other at their distal ends.

5. The medical device according to claim 1, the medical device further comprising a plurality of shape memory alloy wires extending at least partially along the elongated body, and being fixed at both ends with respect to the elongated body, wherein the plurality of shape memory alloy wires includes the shape memory alloy wire.

6. The medical device according to claim 5,
   wherein the elongated body comprises segments with various stiffness and
   wherein the shape memory alloy wires extend at least partially along two adjacent segments with different stiffness.

7. A deflectable medical device comprising:
   a flexible elongated body having proximal and distal ends and a first lumen:
   a shape memory alloy wire eccentric to the longitudinal axis and extending at least partially along the elongated body, the shape memory alloy wire fixed at least at two distinctive points with respect to the elongated body and arranged to receive energy from an energy supply so as to heat the shape memory alloy wire;
   a fixture in the proximal end of the elongated body; and
   a rod located in the first lumen and extending at least from the fixture to the distal end of the elongated body, the rod fixed with respect to the elongated body between the fixture and the distal end,
   wherein the rod is compressed between the fixture and the distal end of the elongated body,
   wherein the shape memory alloy wire is arranged to shorten upon receiving energy from the energy supply,
   wherein the medical device comprises a resistor connectable to the energy supply and arranged to convert the electrical energy supplied by the energy supply into heat for heating the shape memory alloy wire.

8. A deflectable medical device comprising:
   a flexible elongated body having proximal and distal ends and a first lumen:
   a shape memory alloy wire eccentric to the longitudinal axis and extending at least partially along the elongated body, the shape memory alloy wire fixed at least at two distinctive points with respect to the elongated body and arranged to receive energy from an energy supply so as to heat the shape memory alloy wire;
   a fixture in the proximal end of the elongated body; and
   a rod located in the first lumen and extending at least from the fixture to the distal end of the elongated body, the rod fixed with respect to the elongated body between the fixture and the distal end,
   wherein the rod is compressed between the fixture and the distal end of the elongated body,
   wherein the shape memory alloy wire is arranged to shorten upon receiving energy from the energy supply, and
   wherein the compression of the rod is adjustable through the fixture in the proximal end of the elongated body.

9. A system comprising:
   a deflectable medical device comprising:
      a flexible elongated body having proximal and distal ends and a first lumen;
      a shape memory alloy wire eccentric to the longitudinal axis and extending at least partially along the elongated body, the shape memory alloy wire fixed at least at two distinctive points with respect to the elongated body and arranged to receive energy from an energy supply so as to heat the shape memory alloy wire;
      a fixture in the proximal end of the elongated body; and a rod located in the first lumen and extending at least from the fixture to the distal end of the elongated body, the rod fixed with respect to the elongated body between the fixture and the distal end, wherein the rod is compressed between the fixture and the distal end of the elongated body, wherein the shape memory alloy wire is arranged to shorten upon receiving energy from the energy supply, the energy supply for providing energy to the shape memory alloy wire; and a control unit for controlling the energy supply, wherein the medical device comprises a second lumen in the elongated body, extending at least partially along the shape memory alloy wire, the system further comprising a pump for providing fluid flow in the second lumen.

10. A method for deflecting a medical device, the method comprising:

providing a compression to a rod fixed between a distal end and a fixture in a proximal end of an elongated body of a deflectable medical device, the medical device further comprising multiple shape memory alloy wires eccentric to the longitudinal axis of the elongated body, extending at least partially along the elongated body and being fixed at both ends with respect to the elongated body; and providing energy to the multiple shape memory alloy wires by an energy supply so as to heat the multiple shape memory alloy wires, wherein providing energy to the multiple shape memory alloy wires is arranged such that the shape memory alloy wires receive dissimilar quantities of energy from the energy supply.

11. A method for deflecting a medical device, comprising the method according to claim 10 and providing fluid flow in the elongated body of the medical device.

12. A computer-readable medium having stored a computer-executable program for deflecting a medical device, the computer program comprising program code means for causing a deflectable medical device to carry out the steps for deflection of the medical device according to claim 10, when the computer program is run on a computer of the control unit controlling the deflectable medical device.

* * * * *